United States Patent [19]

Bujard et al.

[11] Patent Number: 4,495,280

[45] Date of Patent: Jan. 22, 1985

[54] CLONED HIGH SIGNAL STRENGTH PROMOTERS

[75] Inventors: Hermann G. Bujard, Heidelberg, Fed. Rep. of Germany; Annie C. Y. Chang, Palo Alto; Stanley N. Cohen, Portola Valley, both of Calif.

[73] Assignee: The Board of Trustees of the Leland Stanford Jr. University, Stanford, Calif.

[21] Appl. No.: 265,276

[22] Filed: May 20, 1981

[51] Int. Cl.³ .......................... C12Q 1/68; C12Q 1/02; C12P 21/00; C12P 19/34; C12N 15/00

[52] U.S. Cl. .......................................... 435/6; 435/29; 435/68; 435/172.3; 435/91; 536/27; 935/6; 935/36; 935/37; 935/41; 935/76

[58] Field of Search .................. 435/29, 68, 6, 172, 435/240, 253, 254, 257, 258, 317, 91; 536/27, 28, 29

[56] References Cited

PUBLICATIONS

Stuber et al., PNAS, 78(1), 167–171, (Jan. 1981).
Casadaban et al., J. Mol. Biol., 138, 179–207, (1980).
West et al., Gene, 9, 175–193, (1980).
Gabain et al., PNAS, 76(1), 189–193, (1979).
Stüber et al., Molec. Gen. Genet., 166, 141–149, (1978).
Stüber et al., PNAS USA, 78(1), 167–171, (1981).

*Primary Examiner*—Esther M. Kepplinger
*Attorney, Agent, or Firm*—Bertram I. Rowland

[57] ABSTRACT

Method for preparing high signal strength promoters and terminators and DNA compositions employing such promoters and terminators. T5 phage is cleaved to provide for DNA sequences having intact promoters. These promoters are inserted into vectors separated from a balanced terminator by a gene of interest and the terminator is desirably followed by a marker allowing for selection of transformants. High efficiencies in transcription of DNA can be achieved with the highly active T5 promoters. The promoters and terminators are used in hybrid DNA for efficient expression of structural genes and transcription to provide RNA sequences.

15 Claims, 1 Drawing Figure

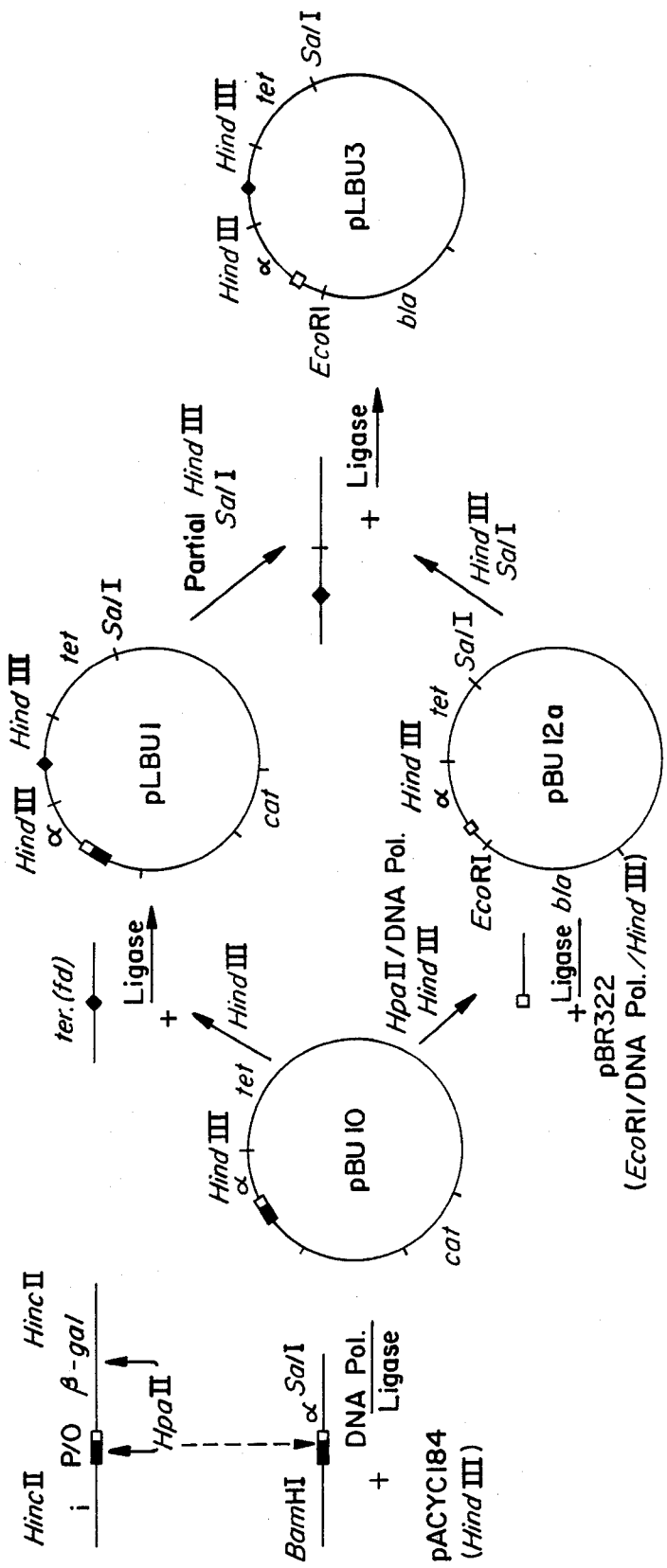

CLONED HIGH SIGNAL STRENGTH PROMOTERS

The government has rights in the invention pursuant to Grant Nos. AI 08619 and GM 27241 awarded by the National Institute of Health.

The research was supported in part by a grant from the Deutsche Forschungsgemeinschaft.

BACKGROUND OF THE INVENTION

1. Field of the Invention

Having established the feasibility of producing a wide variety of naturally occurring and synthetic polypeptides by means of hybrid DNA technology, there are continuing and extensive efforts to provide for more efficient and economic methods for producing the polypeptides. In developing a process for the commercial production of polypeptides, many factors will be involved in optimizing the economic and efficient production of the polypeptides. Included among these factors are regulatory signals, which are DNA sequences involved with the regulation of replicaton, transcription and translation.

One area of interest is at the level of transcription. Transcription involves the enzyme RNA polymerase. The RNA polymerase binds to a site called a promoter. It has been observed that promoters vary in their activity, as evidenced by the number of initiations of RNA per unit time or the strength of binding of the enzyme to the promoter site. The promoter may have one or more sequences that bind, which may or may not be contiguous. The more active promoters are referred to as strong promoters.

It was found that when introducing a strong promoter into a vector and employing the resulting plasmid for transformation, one could not select transformants based on expression of markers which allowed for selection. Therefore, cloning of the strong promoters was not feasible. It is therefore desirable that methods be provided which would allow for the screening of strong promoters and terminators and their subsequent cloning to be used in conjunction with the replication, transcription and translation of the genes for production of DNA, RNA, and polypeptides.

2. Description of the Prior Art

Promoters from bacterial and viral sources have been cloned in *E. coli*, and their signal strength in vitro has been studied using expression from distal promoterless sequences encoding β-galactosidase or other proteins (Casadaban and Cohen (1980) J. Mol. Biol 138, 179–207; West and Rodriguez (1980) Gene 9, 175–193). Attempts to clone small DNA fragments carrying the strong promoters of bacteriophage T5 have been unsuccessful (v. Gabain and Bujard (1979) PNAS USA 76, 189, 193), Fragments of T5 DNA having both a strong promoter and a strong termination signal have been cloned. (Breunig (1979) Dissertation (Universitat Heidelberg, Heidelberg, Germany)) Analysis has shown that transcriptional regions of several *E. coli* plasmids are organized in units where initiation and termination signals, are balanced. (Stuber and Bujard (1981) PNAS USA 78: 167–171) $P_{25}$ and $P_{26}$ promoters of the T5 bacteriophage are reported as among the most efficient RNA polymerase binding sequences. (Stuber et al (1978) Mol. gen. Genet. 166 141–149; Niemann (1981) Diplomarbeit (Universitat Heidelberg, Heidelberg, Germany)).

SUMMARY OF THE INVENTION

Methods for cloning, sequencing and using strong promoters and terminators are provided, as well as compositions resulting from the methods. By cleaving T5 phage and selecting fragments specifically binding to RNA polymerase, fragments containing promoters are isolated. A vector is constructed having a strong promoter, followed by a DNA sequence of interest, optionally followed by one or more translational stop codons in one or more reading frames, followed by a balanced terminator, followed by a marker allowing for selection of transformants. Upon introducing the resulting plasmid into a microorganism host, efficient transcription of the gene is obtained with substantially lesser expression of the marker as compared to the gene. The level of expression of the marker permits selection of transformants having the above described construct. The construct or regulatory portions thereof are used for efficient transcription of RNA or gene expression.

BRIEF DESCRIPTION OF THE DRAWING

FIG. 1 is a flow chart of the preparation of a plasmid for cloning strong promoters and terminators.

DESCRIPTION OF THE SPECIFIC EMBODIMENTS

Methods and compositions are provided for preparing and cloning strong promoter and terminator regulatory signals and utilization of the strong regulatory sequences in the transcription and expression of genes of interest.

Particularly, T5 phage promoters are isolated, cloned in conjunction with a strong terminator, and appropriate vectors developed for insertion of DNA sequences of interest, usually structual genes, to provide for high and efficient transcription and/or expression of the sequence.

The compositions of this invention are characterized as having in the downstream direction of transcription the following units: a strong T5 phage promoter; optionally a structural gene which may be a marker; a balancing terminator; and optionally a marker allowing for selection of transformants containing the construct, which marker has a relatively low level of expression in comparison with the amount of RNA polymerase initiation at the promoter. In the absence of a promoter in the construct, the construct can be used for the cloning and characterization of promoters of different strengths.

In referring to strong promoters, it is intended that the binding affinity of RNA polymerase is stronger than the commonly employed promoters such as lac and trp and at least comparable to and normally greater than the combination of lac and trp promoters. For the most part, the strongest promoters among prokaryotes are the T5 phage promoters and these will be employed as exemplary of naturally occurring or synthetic strong promoters. It is to be understood, that other prokaryotic and eukaryotic promoters, either naturally occurring or synthetic, could find application in the subject invention.

The compositions of this invention will include linear segments for insertion of DNA having the strong regulatory signal sequences (i.e., the promoter and terminator) adjacent opposite ends of the linear segment and plasmids formed by introducing a DNA sequence from a source other than the source of the promoter as a bridge between the strong regulatory signal sequences.

The termini may be blunt or staggered ended, having the same or different termini to allow for directed positioning of inserted sequences.

The compositions which are employed as already indicated have a promoter, a balanced terminator, and desirably a marker which are in the direction of transcription when the signal sequences are joined. The terminator is balanced, so that a small but useful amount of expression of the marker can occur. Normally, in most situations, a gene will bridge the promoter and terminator to provide circular DNA. The gene may be a non-structural gene or a structural gene providing RNA e.g. ribosomal or messenger, or providing a poly(amino acid).

Desirably, the gene is followed by one or a plurality of translational stop codons e.g. oop or nonsense codons, or preferably a plurality, usually up to about six, more usually from about two to five, where there is at least one stop codon in each reading frame. The stop codons aid in the efficiency of termination, both at the level of transcription and expression.

Next in the direction of transcription is the terminator sequence. The terminator sequence is balanced with the promoter in the sense that the marker is transcribed not more than about one-fourth of the times that a gene upstream from the terminator is transcribed, where both genes are under the control of the same promoter. Usually, it will be desirable that a sufficient amount of the marker is transcribed to allow for selection of transformants. In view of the fact that the marker is transcribed from a strong promoter, it will usually be sufficient that the marker is transcribed in relation to the transcription of the gene intermediate the promoter and terminator in only about 1 to 20, usually only 5 to 15 number % of the gene. The strength of the promoter is reflected in the level of expression of the marker which is transcribed from the same promoter as the gene whose expression is desired.

In addition to the DNA sequences indicated above, there will normally be other regulatory signals necessary for expression involved with the DNA sequence, such as translational start and stop sites. In addition to the foregoing regulatory signals, other regulatory signals may be included, such as additional promoters, operators, initiators, catabolite activator protein binding sites, etc. Furthermore, the promoter and terminator may be separated by more than one gene, that is, a plurality of genes, including multimers and operons.

The above DNA sequence construct will have a replicating system or be cleaved and be inserted into a vector to provide a plasmid. The vector is distinguished by having one or more DNA sequences which serve to insure stable replication of the plasmid and may also provide opportunities for high copy numbers of the plasmid in the microorganism host. The vectors may be derived from chromosomal or extrachromosomal sources. The sources include plasmids, viruses (phage), chromosomes, or the like. In addition, the vector or the essential portions thereof may be prepared synthetically.

The plasmids may then be used for transformation of an appropriate microorganism host. Methods of introducing DNA into an appropriate host are well known. Illustrative of such methods, but not exhaustive of such methods, are transformation e.g. calcium shock, transfection, and conjugation. Descriptions of these methods may be found in Genetic Engineering, ed. Setlaw and Hollaender, Vol. 1, Plenum Press, New York and London, 1979; Molecular Cloning of Recombinant DNA, ed. Scott and Werner, Vol. 13, Academic Press, Inc. New York, 1973, and references cited therein.

In order to allow for flexibility in preparing the construct and self-replicating sequence or plasmid containing the construct restriction sites should be present to allow for unique insertions and isolation of the various elements. The restriction sites may be naturally present, introduced by linkers, result by partial sequential nucleotide removal from a chain using an exonuclease, or the like. Desirably, the restriction sites will provide for different ends to permit only the proper orientation of the inserted fragment.

A wide variety of structural genes are of interest for production of proteins, including but not limited to proteins of physiological interest, proteins as chemicals, and enzymes which may be of direct interest or of interest in transforming another product, which may be proteinaceous or non-proteinaceous. The proteins may be prepared as a single unit or as individual subunits and then joined together in appropriate ways. Furthermore, as appropriate, the protein products may be modified by glycosylation, acylation with aliphatic acids, e.g. lipid acids, phosphorolation, sulfonation or the like. The different classes of proteins which may be prepared include protamines, histones, albumins globulins, scleroproteins, phosphoproteins, mucoproteins, chromoproteins, lipoproteins, nucleoproteins, and the remaining proteins which are unclassified.

The following is a representative list of proteins of interest.

Insulin; growth hormone; interferon e.g. leukocyte, lumphoblastoid, T-immune and fibroblast; $\beta$-lipotropin; $\beta$-endorphin; dynorphin; histocompatability proteins; immunoglobulins e.g. IgA, IgD, IgE, IgG and IgM and fragments thereof; hemoglobin, somatomedins; lymphokines; growth factors e.g. epidermal, fibroblast, platelet-derived, multiplication stimulating and nerve; hematoporetic-stimulating factors e.g. erythropoietin, colony-stimulating, erythroid potentating activity or burst-promoting activity and lymphopoietins; albumin and prealbumin;
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
$\alpha_1$-glycoprotein
$\alpha_1$-$\chi$-Glycoprotein
Thyroxin-binding globulin
Inter-$\alpha$-trypsin-inhibitor
Gc-globulin:
 (Gc 1-1),
 (Gc 2-1),
 (Gc 2-2),
Haptoglobin:
 (Hp 1-1),
 (Hp 2-1),
 (Hp 2-2),
Ceruloplasmin
Cholinesterase
$\alpha_2$-Lipoprotein(s)
$\alpha_2$-Macroglobulin
$\alpha_2$-HS-Glycoprotein Zn-$\alpha_2$-glycoprotein
$\alpha_2$-Neuramino-glycoprotein
  Erythropoietin
$\beta$-lipoprotein
  Transferrin
  Hemopexin
  Fibrinogen
  Plasminogen
$\alpha_2$-glycoprotein I
$\alpha_2$-glycoprotein II
  Immunoglobulin G
    (IgG) or $\gamma$G-globulin
  Mol. formula:
    $\gamma_2\kappa_2$ or $\gamma_2\lambda_2$
  Immunoglobulin A (IgA) or $\gamma$A-globulin
  Mol. formula:
    $(\alpha_2\kappa_2)^n$ or $(\alpha_2\lambda_2)^n$
  Immunoglobulin M (IgM) or $\gamma$M-globulin
  Mol. formula:
    $(\mu_2\kappa_2)^5$ or $(\mu_2\lambda_2)^5$
  Immunoglobulin D (IgD) or $\gamma$D-Globulin ($\gamma$D)
  Mol. formula:
    $(\delta_2\kappa_2)$ or $(\delta_2\lambda_2)$
  Immunoglobulin E (IgE) or $\gamma$E-Globulin ($\gamma$E)
  Mol. formula:
    $(\epsilon_2\kappa_2)$ or $(\epsilon_2\lambda_2)$
  Free light chains
  Complement factors:
  C'1
    C'1q
    C'1r
    C'1s
  C'2
    $\beta_1$A
$\alpha_2$D
  C'4
  C'5
  C'6
  C'7
  C'8
  C'9.
Important protein hormones include:

Peptide and Protein Hormones

Parathyroid hormone: (parathormone)
Thyrocalcitonin
Insulin
Glucagon
Relaxin
Erythropoietin
Melanotropin: (Melanocyte-stimulating hormone; intermedin)
Somatotropin: (growth hormone)
Corticotropin: (adrenocorticotropic hormone)
Thyrotropin
Follicle-stimulating hormone
Leuteinizing hormone: (interstitial cell-simulating hormone)
Luteomammotropic hormone: (Luteotropin, prolactin)
Gonadotropin: (chorionic gonadotropin).

Tissue Hormones

Secretin
Gastrin
Angiotensin I and II
Bradykinin
Human placental lactogen

Peptide Hormones from the Neurohypophysis

Oxytocin
Vasopressin
Releasing factors (RF): CRF, LRF, TRF, Somatotropin-RF, GRF, FSHRF, PIF, MIF.

In addition to various non-enzymatic proteins of physiological interest, enzymes can also be produced as an end product or for intracellular transformation of a substrate present in the host or substrate introduced extracellularly, or for enzymatic transformation in vitro.

In accordance with the I.U.B. classification, the enzymes fall into varying categories such as 1. oxidoreductases; 2. transferases; 3. hydrolases; 4. lyases; 5. isomerases; 6. ligases. Enzymes of particular interest will be hydrolases and oxidoreductases for use in commercial processing, for example, hydrolases for hydrolysing polysaccharides, lipids and polypeptides; oxidoreductases for oxidation of alcohols and aldehydes, epoxidation, and the like.

The microorganism host may be bacteria, such as Escherichia, Bacillus, Aerobacter, Klebsiella, Proteus, Pseudomonas, Streptococcus, Staphylococcus, Clostridium, Mycobacterium, Streptomyces and Actinomyces; Fungi e.g. Gymnomycota, Dimastygomycota, Eumycota, Zygomycetes, Ascomycetes and Basidomycetes, such as, Candida, Aspergillus, Rhizobus, Microsporum, and Fonsecaea; Protozoa e.g. Mastigophora, Sarcodina, Sporozoa and Celiophora, such as, Trypanosoma, Codosiga, Protospongra and Entameba, and Alga e.g. Dinoflagellates, Euglenoids, and Diatoms.

Higher cells, e.g., mammalian, may also be employed as hosts, where viral, e.g., bovine papilloma virus or other DNA sequence is available which has plasmid-like activity.

Depending upon the nature of the host, a wide variety of vectors may be employed. The vector will have an intact replicon and be capable of replication in the host. In addition, replicons can be developed which may have one or more other regulatory signals. Regulatory signals can include temperature sensitive replicons, runaway-replication sequences, temperature sensitive operators, and the like. Various additional DNA sequences may be present providing for restriction sites, markers, termination sequences, or the like. Desirably, the vector should be of a substantially different size from the construct to allow for excision of the construct and ease of separation of the construct from the vector by molecular weight separation techniques e.g. electrophoresis and density gradient centrifugation.

The subject invention also provides for a technique for screening the strength of promoters and terminators, thus allowing for the determination of the use of a promoter or terminator in a particular application, where it may be desirable to have promoters or terminators or combinations thereof of varying strength. In screening promoters and/or terminators one employs a promoter or terminator of known activity. A DNA construct is made having the sequence described previously, where appropriate restriction sites are provided for introducing the various elements. The construct provides in the direction of transcription the promoter, a first gene marker, optionally termination codons, such as nonsense codons and oop terminator, the terminator, and a second gene marker. This DNA construct is inserted into an appropriate vector. Where the promoter and terminator are properly balanced, there will be a substantial differentiation between expression of the first gene marker and expression of the second gene marker. The ratio of expression between the first and second marker will provide for a comparative evaluation of the activity of the promoter or terminator, depending upon which is of known value. Thus, one can degrade a DNA sequence such as a chromosome, or an extrachromosomal element, such as a plasmid or double minute, isolate the promoters by selective binding with RNA polymerase and insert the DNA fragments which bind to the RNA polymerase into the previously described construction. By determining the relative proportion of expression of the first and second gene markers, one can determine the strength of promoters in relation to a fixed terminator. Similarly, one can isolate DNA sequences having terminator sequences, insert the sequences into the above described construct at the appropriate site and then measure the relative expression of the two gene markers.

Various markers can be chosen for evaluating the relative activities of promoters and terminators. Conveniently, markers which allow for selection such as resistance to antibiotics, toxins or heavy metals can be used. By varying the concentration of the selective agents in the nutrient medium, one can determine the relative proportions of the enzyme expressed by the genes in relation to the growth of the host. Alternatively, one can use growth factors e.g. having a gene which complements a mutant gene in an auxotrophic host, where the gene expresses a product necessary for a biosynthetic pathway. A third marker provides virus incompatibility, preventing plaque formation. Other markers which allow for comparison will come readily to mind.

The terminators may be evaluated in the presence and absence of rho, so that one can determine the dependency of the terminator on rho, as well as the effectiveness of the terminator in relation to the concentration of rho.

The methods for preparing the subject compositions will be conventional. The various DNA fragments and sequences can be obtained from a variety of sources by restriction mapping and endonuclease cleavage to provide fragments having the desired intact sequence or gene. The fragments can be further processed employing endo- or exonucleases to remove nucleotides unrelated to desired regulatory sequences or structural genes. By appropriate choice of restriction enzymes, cohesive or blunt ended fragments can be generated. Furthermore, chains can be extended with single nucleotides or oligonucleotides, linkers can be added, or otherwise processing to provide for termini having desired properties.

Desirably, a vector is employed having appropriate restriction sites, a competent replication system for the intended host, and optionally one or more markers which allow for selection. For hybrid DNA technology it would be useful to have a plasmid having a unique restriction site between a T5 promoter and a terminator, desirably having at least one stop codon on the upstream side of the terminator. In this manner, one or more structural genes may be introduced between the promoter and terminator.

As appropriate, downstream from the promoter, but remaining proximal to the promoter, may be an operator, activator, ribosomal start signal sequence, or the like, to allow for controlled expression of the inserted gene(s).

The strategy described above provides a vehicle which can be used with one or more hosts for gene expression, where the gene after processing in a predetermined way can be directly inserted into the vehicle to provide a competent plasmid for expression of the desired gene(s).

Alternatively, the gene(s) of interest may be ligated to the appropriate regulatory signal sequences before insertion into the vehicle. In this instance, only the promoter and terminator regulatory signals need be present.

To provide for enhanced flexibility, the region between the promoter and terminator may be designed so as to provide for a plurality of restriction cleavage sites, allowing for the introduction and removal of DNA fragments without interruption of the remainder of the vehicle. Thus, by having a plurality of unique restriction sites or restriction sites limited to the region between the promoter and terminator in the downstream direction of transcription, regulatory signals and genes may be readily inserted and removed.

Another strategy is to prepare a construct having all of the desired DNA sequences for transcription and expression in appropriate sequence, with the construct having predetermined termini and inserting the construct into an appropriate vector which has been linearized to provide complementary termini.

In developing the construct, a vector will normally be used in order to clone the various sequences. The construct will allow for the insertion of the different sequences in the correct direction and desirably only in the proper orientation. Therefore, it will usually be desirable to have the sequence and insertion site be asymmetric in having different termini with the termini of the sequence and insertion site being complementary.

The particular restriction enzymes will vary widely with the various sequences, there being a large number of restriction enzymes of known base or sequence specificities commercially available.

The following examples are offered by way of illustration and not by way of limitation.

EXPERIMENTAL

Materials and Methods

Restriction endonucleases HindIII, HincII, SalI, BamHI and T4 Ligase were from New England Biolabs (Beverly, Mass., USA), Sau3A was from BRL (Neu-Isenburg, Germany) and EcoRI and HpaII from (Boehringer Mannheim, Federal Republic of Germany). DNA polymerase I, phage fd DNA (replicative form), plasmid AD16/30 containing a 28 bp HindIII/BamHI adapter sequence and, lac represser were supplied by private sources. The isolation of bacteriophage T5 DNA, plasmid DNA E. coli RNA polymerase and E. coli termination factor rho have been described previously, (v. Gabian and Bujard, Mol. gen. Genet. (1977) 157, 301–311; Clewel and Helinski (1969) PNAS USA 62, 1157–1166; and Knopf and Bujard (1975) Eur. J. Biochem. 53, 371–385).

A 780bp DNA fragment carrying the E. coli lac regulatory region (promoter/operator: P/O), an N-terminal portion of the β-galactosidase structural gene sufficient for intracistronic complementation of the M15 deletion, as well as a portion of the i-gene(i) was isolated from a HincII digest of a pACYC 214 plasmid (a plasmid related to pACYC 184 by insertion at a BamHI site of a BamHI restriction cleavage fragment from F'-lac carrying the lac gene) by repressor binding and subsequent adsorption to nitrocellose. This fragment was then employed in the construction of an exemplary plasmid for analyzing strong promoters and strong terminators as depicted in FIG. 1.

Utilizing the HpaII cleavage site within the β-gal structural genes the fragment was reduced in size and provided with BamHI and SalI cleavage sites by various subcloning. The resulting fragment (left most part of Figure) contains the intact control region of the lac operon and an N-terminal portion of the β-gal structural gene coding for 66 amino acids (α). Introduction of this fragment by blunt end ligation into the HindIII site of pACYC184 (Chang and Cohen (1978) J. Bacteriol. 134, 1141–1156) yielded pBU10, a vector suitable for terminator cloning. The major terminator of the coliphage fd genome was isolated as a 338bp Sau3A fragment (Beck et al. (1978) Nucl. Acids Res. 5, 4495–4503), ligated with a BamHI/HindIII adaptor sequence and integrated into pBU10 to yield pLBU1.

Cleavage of the lac sequence in pBU10 by HpaII destroys the lac promoter and liberates upon cleavage with HindIII a fragment containing the lac operator and a region coding for a functional α-fragment. Integrating this DNA sequence into pBR322 leads to pBU12a. Finally, replacement of the HindIII/SalI portion of pBU12a by a partial digest of the HindIII/SalI fragment of pLBU1 containing the fd terminator resulted in pLBU3, a vector suitable for integration of efficient promoters at the EcoRI site. The regions encoding chloramphenicol (Cm), ampicillin (Ap) and tetracycline (Tc) resistance are indicated as cat, bla and tet respectively.

The plasmid, pBU10, had the following properties: (i) it contains the α fragment of β-galactosidase (α-protein) and complemented the M15 deletion of the lac operon; (ii) the Tc resistance it specified was under the control of the lac promoter, as shown in M15 I$^q$ strains; (iii) the HindIII site between the lac gene fragment and the tet gene was restored; the stop codon immediately following the HindIII site limited the length of the lacZ gene product to 68 amino acids.

Insertion of the fd terminator upstream to the tet gene resulted in a 90% reduction in the level of Tc resistance, but no detectable change in the levels of β-galactosidase activity in M15 deletion strains. The results obtained as to the properties imparted to various E. coli strains by various plasmids is set forth in the following table:

Seven independent plasmid isolates from clones contained the expected 352bp HindIII-generated fragment containing the fd terminator. Electrophoretic analysis of all seven BamHI-cleaved isolates and DNA sequence analysis of one of these showed that in all instances the fd terminator had been integrated in an orientation opposite the direction of transcription within the fd phage genome. Sequence analysis also revealed a translational stop codon in frame with the α-protein less than 10bp down stream from the HindIII cleavage forming the conjunction between the lac-derived segment and the fd-derived DNA fragment; a translational stop signal on this position would be expected to result in an α-fragment containing 71 amino acids.

For the cloning of exogenous promoters, the lac promoter on the lac/tet construct had to be removed or destroyed in such a way that a site for the subsequent integration of promoters was retained. To do this, the HpaII cleavage site at position −17 of lac was employed, as described above. Colonies that showed both a reduced level of Tc resistance and the presence of a lac operator sequence, which could be detected on the multicopy plasmid by its ability to bind the lac repressor and induce chromosomal β-gal synthesis, were identified. Endonuclease analysis (HindIII/EcoRI double digest) of plasmids recovered from several isolates yielded two types of vectors: one of these represented by pBU12 harbored the expected 253bp lac fragment; the other represented by pBU12a yielded a 420bp fragment. DNA sequence analysis showed that in pBU12a, a 160bp fragment of unknown origin, containing two to three stop codons in each of the possible translational reading frames, had been integrated between the EcoRI site and position −15 of the lac promoter. The presence of the stop codons made the fragment an efficient terminator of any translation that occurred upstream of the translational initiation site for the α-fragment.

When the HindIII/SalI segment of pBU12a was replaced with an identically generated fragment of pLBU1 carrying the fd terminator, the plasmid pLBU3 was obtained, which conferred neither Tc resistance nor β-gal activity to E. coli M15 strain. Although this plasmid contained a tet region and a DNA sequence encoding the α-fragment of lac, it conferred neither resistance nor β-gal activity to the E. coli M15 strain. It was therefore chosen as the T5 promoter cloning vehicle.

A population of about 200 short fragments of T5 DNA was obtained by double digestion of the 120kb phage genome with HaeIII and AluI endonucleases. These fragments were ligated with excess synthetic EcoRI links and the resulting molecules were cleaved with EcoRI endonuclease and ligated into the EcoRI cleavage site of pLBU3. Transformation of E. coli C600 and selection for β-gal activity plus high level Tc-resistance yielded 35 colonies resistant to Tc-concentrations between 8 and 70 μg/ml. Plasmids were isolated from 13 colonies resistant to 70 μg/ml, which earlier experiments using multicopy plasmids had suggested was the highest level detectable in E. coli K12 (Cabello et al. (1976) Nature 259, 285–290).

Digestion of the various isolates with EcoRI endonuclease liberated between one and ten fragments of various sizes from each constructed plasmid. Complexing of such fragment mixtures with RNA polymerase, followed by filter binding analysis, identified between one and three fragments of each plasmid that interacted very efficiently with the enzyme; these fragments were isolated from polyacrylamide gels and individually recloned in pLBU3. In each case, they gave rise to colonies resistant to 70 μg/ml Tc. Plasmids isolated from each of these clones carried the expected DNA fragments, as shown by EcoRI cleavage and gel electrophoresis. The promoter library which was obtained contained about 25 different strong promoters of coliphage T5.

A plasmid pGBU207 containing an EcoRI-generated fragment of 212bp was selected for further study. In vitro transcription on the plasmid was mapped by analysis of RNA transcripts made on fragments of the plasmid produced by cleavage with different restriction endonucleases. Cleavage of the plasmid with EcoRI endonuclease yielded principally a single RNA species about 130 nt in length. The size of the transcript increased to 550 nt when a HindIII digest of pGBU207 was used as a template. BamHI digested DNA yielded transcripts of about 740 and 900 nt in length. Correlation of transcript length with the distance of the DNA cleavage site from a fixed point insert indicated that in all of these instances in vitro transcription was initiated at the same promoter and that it progressed toward the tet region of the plasmid. The experiments also showed the functioning of the termination signal introduced between the lac fragment and the tet gene. Under the high salt conditions used for this in vitro transcription experiment, termination of about 50% of transcription within the fd DNA fragment gave rise to the 740 nt transcript, while a read-through transcript extended to the BamHI cleavage site located 890bp from the promoter. The data strongly suggested that RNA termination occurring in the fd terminator placed in the reverse orientation is rho dependent, in contrast to the rho-independent termination that occurs when the terminator is in its normal orientation.

Since the rate of complex formation between RNA polymerase and promoter signals is a reflection of the strength of the promoter, the relative rate of complex formation of the 212bp fragment of pGBU207 was compared with complex formation involving the previously studied T5 promoters $P_{25}$ and $P_{26}$ (Stuber and Bujard (1981), supra). The results showed that the promoter used to express downstream genetic functions in pGBU207 has a signal strength similar to that of $P_{25}$ and $P_{26}$, which are among the most efficient RNA polymerase binding sequences identified from any source. (Niemann (1981), supra).

The above results demonstrate that novel DNA sequences can be prepared from the strong T5 promoters, which can then be used for the expression of a wide variety of poly(amino acids). Furthermore, by employing a promoter, optionally a structural gene, a terminator, and a marker, test plasmid structures are provided which allow for screening of the effectiveness of a promoter and/or a terminator, particularly as they interrelate with each other. Therefore, combinations can be prepared which allow for highly efficient transcription of a wide variety of structural genes, with concommitant selection of the transformants by employing an appropriate marker downstream from the balanced terminator.

Although the foregoing invention has been described in some detail by way of illustration and example for purposes of clarity of understanding, it will be obvious that certain changes and modifications may be practiced within the scope of the appended claims.

We claim:

1. A linear DNA sequence having proximal to one end a strong T5 phage promoter, proximal to the other end a strong transcriptional terminator balanced with said strong T5 promoter, and having intermediate said promoter and terminator at least one of (1) a marker for selection adjacent to said terminator or (2) a replication system foreign to T5, wherein the direction of said promoter is away from said terminator and said marker is expressed at a frequency of less than about one-fourth the frequency of a structural gene, when said structural gene is inserted between said promoter and terminator, so as to be under the transcriptional control of said promoter and to bridge said linear DNA sequence to provide a circular DNA sequence.

2. A linear DNA sequence according to claim 1, having intermediate said other end and said strong terminator at least one stop codon in at least one reading frame.

3. A linear DNA sequence according to claim 2, having a plurality of stop codons with at least one in each reading frame.

4. A linear DNA sequence according to any of claims 1, 2 or 3, wherein said marker is a gene imparting biocidal resistance.

5. A linear DNA sequence according to any of claims 1, 2 or 3, wherein said marker is a DNA sequence having at least one gene in a metabolic synthetic pathway.

6. A linear DNA sequence according to any of claims 1, 2 or 3, having a marker intermediate said promoter and said terminator.

7. A linear DNA sequence according to claim 6, wherein said marker provides biocidal resistance.

8. A linear DNA sequence according to claim 6, wherein said marker has at least one gene for an enzyme in a metabolic synthetic pathway.

9. A linear DNA sequence according to any of claims 1, 2 or 3, wherein said replication system is for a prokaryote.

10. A linear DNA sequence according to any of claims 1, 2 or 3, wherein said replication system is for a eukaryote.

11. A method for determining the strength of a promoter which comprises:
    inserting said promoter into a linear DNA sequence having in the downstream direction for expression proximal to one end; a gene allowing for detection of expression; a transcriptional terminator of known strength; a marker allowing for determination of expression; and a replication system recognized by a predetermined host; whereby a circular DNA sequence is obtained;
    transforming said host with said circular DNA sequence;
    growing said host in nutrient medium under conditions allowing for determination of the extent of expression of said gene and said marker; and
    determining the strength of said promoter is determined by the relative degree of transcription of said gene and said marker.

12. A method according to claim 11, wherein said host is auxotrophic and said gene provides prototrophy.

13. A method according to any of claims 11 or 12, wherein said marker provides biocidal resistance.

14. A method according to claim 13, wherein intermediate said gene and said terminator are a plurality of stop codons, with at least one stop codon in each reading frame.

15. A circular DNA sequence having in downstream order of transcription a strong T5 phage promoter, a structural gene foreign to T5 phage under transcriptional control of said promoter, a transcriptional terminator which is balanced with said promoter and a replication system and having a marker for selection downstream from said terminator, wherein said marker is expressed at a frequency of less than about one-fourth the frequency of which the structural gene is expressed and is under transcriptional control of said promoter.

* * * * *